US00PP27185P3

(12) United States Plant Patent
Kordes

(10) Patent No.: US PP27,185 P3
(45) Date of Patent: Sep. 27, 2016

(54) MINIATURE ROSE PLANT NAMED 'KORPOT044'

(50) Latin Name: *Rosa hybrida*
Varietal Denomination: KORpot044

(71) Applicant: W. KORDES' SÖHNE ROSENSCHULEN GMBH & CO KG, Offenseth-Sparrieshoop (DE)

(72) Inventor: Tim-Hermann Kordes, Offenseth-Sparrieshoop (DE)

(73) Assignee: W. KORDES' SÖHNE ROSENSCHULEN GMBH & CO KG, Offenseth-Sparrieshoop (DE)

( * ) Notice: Subject to any disclaimer, the term of this patent is extended or adjusted under 35 U.S.C. 154(b) by 107 days.

(21) Appl. No.: 14/544,595

(22) Filed: Jan. 26, 2015

(65) Prior Publication Data

US 2015/0216094 P1 Jul. 30, 2015

Related U.S. Application Data

(60) Provisional application No. 61/965,414, filed on Jan. 29, 2014.

(51) Int. Cl.
*A01H 5/02* (2006.01)

(52) U.S. Cl.
USPC ..... Plt./117

(58) Field of Classification Search
USPC ..... Plt./116, 117
See application file for complete search history.

*Primary Examiner* — Susan McCormick Ewoldt
(74) *Attorney, Agent, or Firm* — James M. Weatherly; Barbara Campbell; Cochran Freund & Young, LLC

(57) ABSTRACT

A new and distinct variety of rose having long lasting, novel white flowers, and attractive foliage with good disease resistance; exhibiting compact, upright to bushy growth with abundant flowers; propagating well from cuttings and by grafting, is disclosed.

2 Drawing Sheets

Genus and species: *Rosa hybrida.*
Denomination: 'KORpot044'.

BACKGROUND

'KORpot044' originated from a controlled crossing in a breeding program of two distinct parents during the summer of 2010 in a controlled environment in Offenseth-Sparrieshoop, Germany between an un-named *Rosa hybrida* seedling as the seed or female parent (unpatented) and another un-named *Rosa hybrida* seedling as the pollen or male parent (unpatented).

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

The resulting seeds from the cross were planted during the following winter in 2010 and were evaluated. The resulting seedlings exhibited distinctive physical and biological characteristics. 'KORpot044' was selected in April 2011 as a single plant from the seedling beds in Offenseth-Sparrieshoop, Germany due to its superior characteristics. 'KORpot044' was first asexually propagated by rooting softwood cuttings in June 2011 in Offenseth-Sparrieshoop, Germany and asexually propagated for further evaluation. This new and distinctive rose variety was subsequently named 'KORpot044'.

The initial and other subsequent asexual propagations were conducted in controlled environments and demonstrate that 'KORpot044' reproduces true to type in successive generations of asexual reproduction via rooting softwood cuttings.

CROSS REFERENCE TO RELATED APPLICATION

Plant Breeder's Rights for 'KORpot044' were applied for in the European Community on Feb. 6, 2014, Application No. 2014/0284. 'KORpot044' has not been made publicly available or sold more than one year prior to the priority date of this application.

SUMMARY

The following are the most outstanding and distinguishing characteristics of this new variety when grown under normal horticultural practices in Jackson County, Oreg.

1. 'KORpot044' has a large number of white, medium sized flowers; and
2. 'KORpot044' has a compact, upright to bushy habit.

DESCRIPTION OF THE PHOTOGRAPHS

This new miniature rose plant is illustrated by the accompanying photographs which shows an overall view of the plant and a close-up of specific parts of the plant. The colors shown are as true as can be reasonably obtained by conventional photographic procedures.

DETAILED DESCRIPTION

Figure 1:
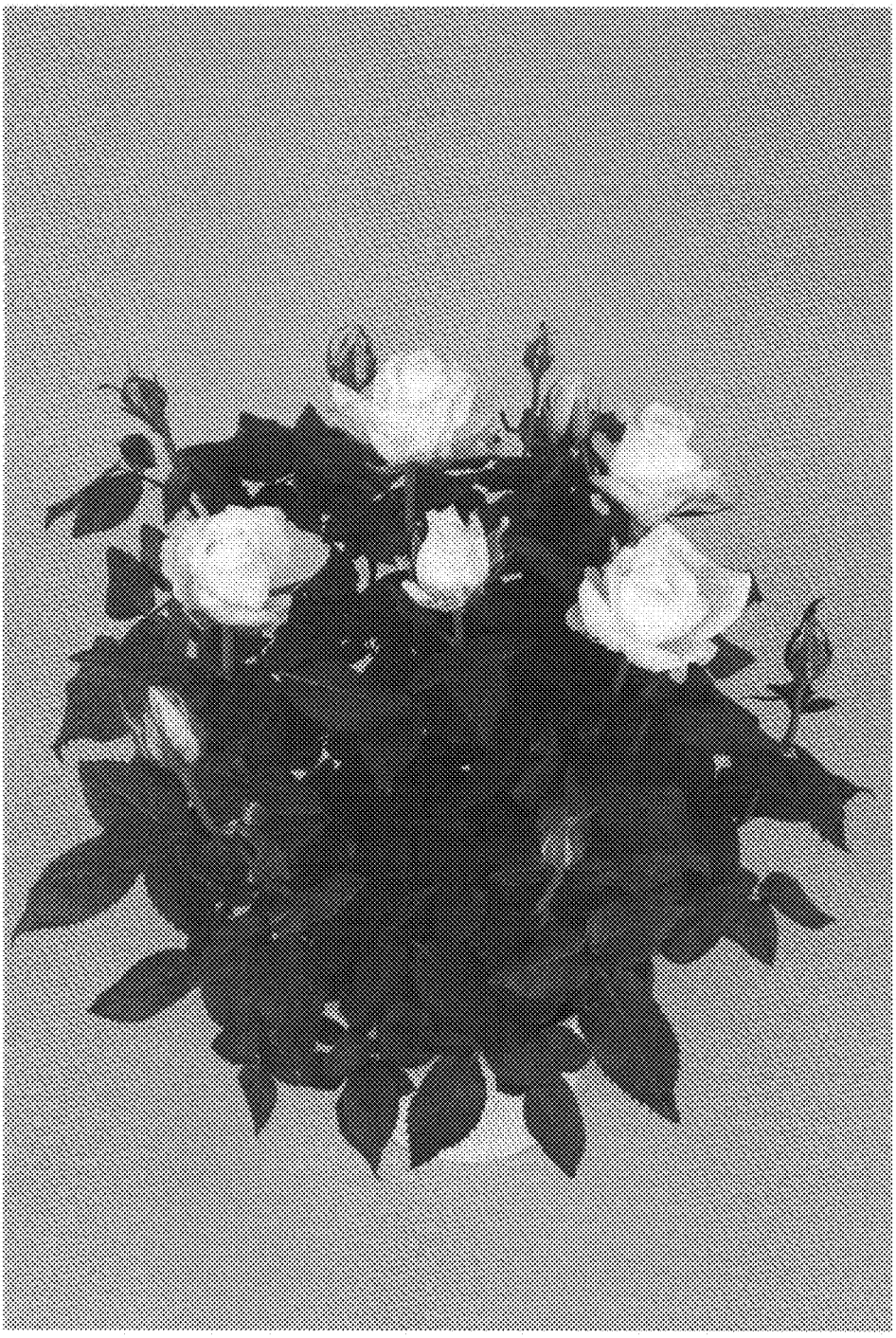
FIG. 1 shows an overall view of 'KORpot044' approximately 4 months of age growing in a glasshouse in the nursery of the breeder in Offenseth-Sparrieshoop, Germany.
Figure 2:
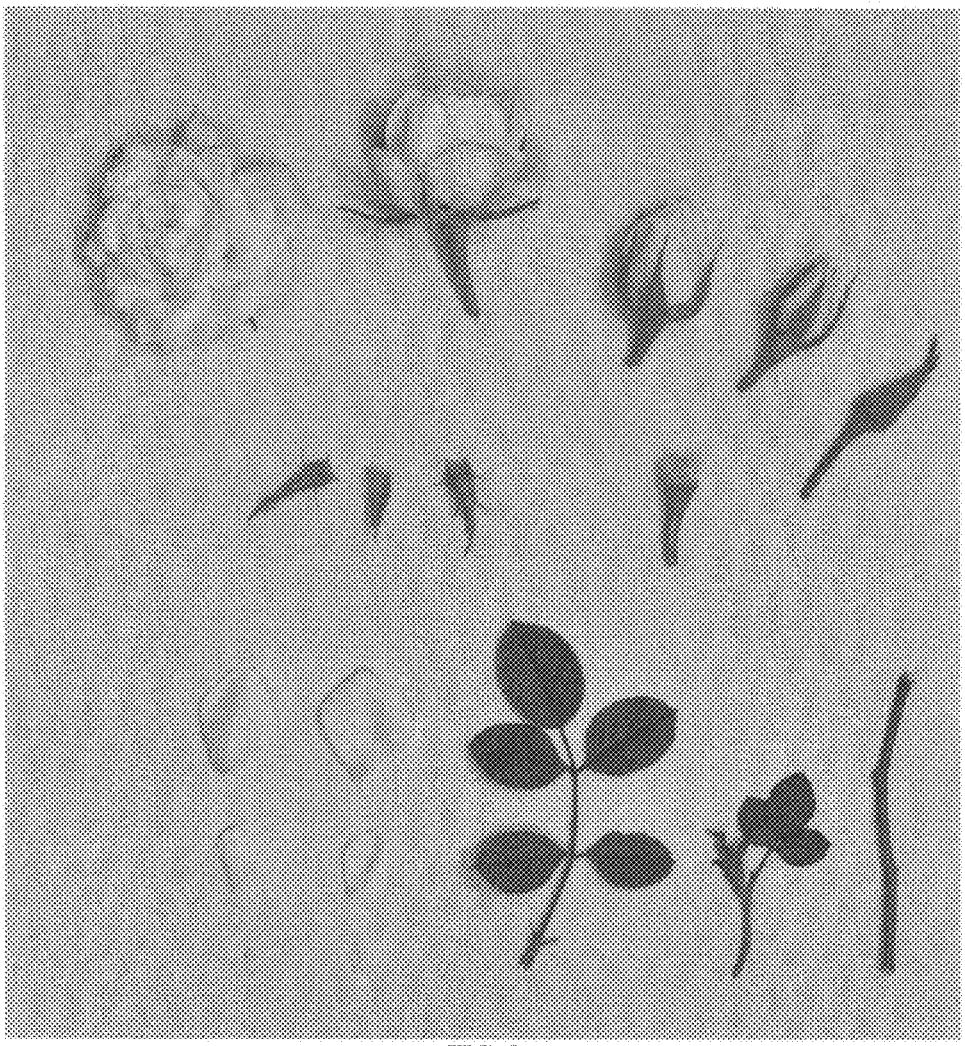
FIG. 2 shows a close-up of the buds, sepals, flowers, leaves, prickles, and stems of 'KORpot044' approximately 6 months of age growing in Jackson City, Oreg.

The following is a description of 'KORpot044', as observed growing in October 2014 in a nursery in Jackson County, Oreg. on plants of 6 months of age. Color references are made using The Royal Horticultural Society (London, England) Colour Chart, 2001 except where common terms of color are used.

Classification:

*Family.*—Rosaceae.

*Species.*—*Rosa hybrida.*

*Common name.*—Miniature rose.

*Variety.*—'KORpot044'.

Parentage:

*Female parent.*—Un-named rose plant (unpatented).

*Male parent.*—Un-named rose plant (unpatented).

Plant:

*Growth.*—Moderately vigorous.

*Habit.*—Compact; upright to bushy.

*Size.*—When grown as a 10.5 cm pot plant, the average plant height is 18.0 cm to 23.0 cm and the average plant width is 15.0 cm to 18.0 cm.

*Winter hardiness.*—Due to the variety's principal use in greenhouses, winter hardiness has not been evaluated.

Stems:

*Color.*—Young wood: RHS 144A (Yellow-Green). Older wood: RHS 146B (Yellow-Green).

*Intonations.*—RHS 183B (Greyed-Red) occasionally present on young wood.

*Stem surface texture.*—Young wood: Smooth. Older wood: Smooth.

*Length.*—16.0 cm to 20.0 cm.

*Diameter.*—2.0 mm to 3.0 mm.

Prickles:

*Quantity.*—Average of 7 per each 10.0 cm of stem.

*Shape.*—Linear.

*Size.*—Average length of large prickles is 3.0 mm.

*Color.*—Immature prickles: RHS 182B (Greyed-Purple). Mature prickles: RHS 145C (Yellow-Green); senescing to 165A (Greyed-Orange).

Leaves:

*General.*—Normally 5 leaflets on normal leaves in middle of the stem.

*Venation pattern.*—Pyramidal net pattern.

*Leaf size.*—90.0 mm in length and 55.0 mm in width.

*Abundance.*—Average.

Leaflets:

*Size.*—Average size of the terminal leaflet is 30.0 mm in length and 20.0 mm in width.

*Shape.*—Elliptic.

*Base.*—Obtuse.

*Apex.*—Acute.

*Margins.*—Finely serrated.

*Surface appearance.*—Semi-glossy.

*Texture.*—Upper surface: Leathery. Lower surface: Leathery.

*Color, mature foliage.*—Upper surface: RHS 137A (Green). Lower surface: RHS 146B (Yellow-Green).

*Color, immature foliage.*—Upper surface: RHS 137A (Green). Lower surface: RHS 147B (Yellow-Green).

*Anthocyanin intonation.*—RHS 183A (Greyed-Purple) present on leaflet margins and lower surfaces of most immature foliage.

*Arrangement.*—Odd pinnate.

*Venation.*—Reticulate.

*Stipules.*—Size: 15.0 mm in length and 3.0 mm in width. Color: RHS 144A (Yellow-Green). Anthocyanin: RHS 182A (Greyed-Red) present on apices and upper surface of midrib. Stipitate glands: Limited numbers of stipitate glands on margins, many fine hairs present on body. Margins: Glandular toothed. Texture: Smooth. Apex: Apiculate. Base: Winged.

*Petiole.*—Length: Average is 25.0 mm to 30.0 mm. Diameter: Average is 1.0 mm. Color: Upper surface: RHS 137A (Yellow-Green). Lower surface: RHS 146A (Yellow-Green). Anthocyanin: RHS 182A (Greyed-Red) present on upper surface. Prickles: A few small prickles underneath. Stipitate glands: Limited numbers of stipitate glands present on margins. Texture: Papillate.

*Petiole rachis.*—Length: Average is 10.0 mm to 20.0 mm. Diameter: Average is 1.0 mm. Color: RHS 137A (Green). Anthocyanin: None observed. Margins: Papillate. Prickles: A few small prickles underneath. Stipitate glands: Limited numbers of stipitate glands on margins and underneath.

Flower bud:

*Size.*—Upon opening, 25.0 mm to 30.0 mm in length from base of receptacle to distal end of bud and 20 mm diameter at its widest point.

*Form.*—Long; pointed ovoid.

*Color.*—As sepals first unfold, bud color is RHS 155A (White). When ¼ open, the upper surface of petals is RHS 155B (White), and the lower surface is RHS 155B (White). Lower surface of outermost petals is RHS 157A (Green-White) with intonations of RHS 144B (Yellow-Green).

Sepals:

*Color.*—Upper surface: RHS 146C (Yellow-Green). Lower surface: RHS 146B (Yellow-Green).

*Size.*—Average is 25.0 mm to 30.0 mm for the length and 6.0 mm to 8.0 mm for the width.

*Shape.*—Weak foliaceous appendages on 3 of the five sepals.

*Apex.*—Apiculate.

*Base.*—Flat at union with receptacle.

*Quantity.*—Five.

*Surface texture.*—Upper side: Hoary. Lower surface: Hoary.

*Margins.*—Cilliate.

*Stipitate glands.*—Limited.

Flower:

*Blooming habit.*—Recurrent; floriferous.

*Borne.*—Singularly. Flowers held upright.

*Fragrance.*—Light.

*Duration.*—On the plant 18 days; senesced petals drop away cleanly.

*Size.*—Medium for a miniature rose. When open, the average flower diameter is 50.0 mm to 60.0 mm and the average flower height is 30.0 mm.

*Shape of flower when viewed from the side.*—Upon opening, upper part: Flat. Upon opening, lower part: Flattened convex. Open flower, upper part: Flat. Open flower, lower part: Flat.

*Color.*—Upon opening, petals: Outermost petals: Outer Side: RHS 155C (White). Inner Side: RHS 155A (White). Innermost petals: Outer Side: RHS 150D (Yellow-Green). Inner Side: RHS 150D (Yellow-Green). After opening, petals: Outermost petals: Outer Side: RHS 155A (White). Inner Side: RHS 155A (White). Innermost petals: Outer Side: RHS 155A (White). Inner Side: RHS 155B (White). Upon opening, basal petal spots: Basal petal spot, outermost petals: Outer Side: RHS 145B (Yellow-Green). Inner Side: RHS 145C (Yellow-Green). Basal petal spot, innermost petals: No distinctive coloration at petal base observed. After opening, basal petal spots: Basal petal spot, outermost petals: Outer Side: RHS 145B (Yellow-Green). Inner Side: RHS 145C (Yellow-Green). Basal petal spot, innermost petals: Outer Side: RHS 150C (Yellow-Green). Inner Side: RHS 150C (Yellow-Green).

*Size.*—Average is 2.0 mm to 4.0 mm in height and 3.0 mm to 5.0 mm in width.

*General tonality.*—On open flowers, RHS 155C (White); no change in the general tonality at the end of the eighth day; afterwards, general tonality is RHS 155B (White).

Petals:

*Petal count.*—Very double; approximately 115 to 120 petals under normal conditions.

*Petal reflex.*—Outermost petals reflex very slightly.

*Shape.*—Outermost petals are obovate and innermost petals are elliptic.

*Apex.*—Outermost petals obtuse and innermost petals are acute.

*Base.*—Outermost and innermost petals are cuneate.

*Margin.*—Entire.

*Petal size.*—10.0 mm to 30.0 mm in length and 5.0 mm to 25.0 mm in width.

*Petal arrangement.*—Not formal.

*Texture.*—Upper and lower surfaces are smooth.

Pedicel: None observed.

Peduncle:

*Surface.*—With fine hairs and stipitate glands.

*Length.*—35.0 mm to 45.0 mm average.

*Diameter.*—2.0 mm to 4.0 mm average.

*Color.*—RHS 144A (Yellow-Green); occasional intonations of RHS 182B (Greyed-Red).

*Strength.*—Strong.

*Texture.*—Papillate.

Petaloids:

*Petaloid count.*—Average of 30 per flower

*Size.*—5.0 mm to 6.0 mm in length and 3.0 mm to 4.0 mm in width.

*Color.*—Upper surface: RHS 150D (Yellow-Green). Lower surface: RHS 150D (Yellow-Green).

*Texture.*—Upper and lower surfaces are smooth.

*Margins.*—Entire.

*Shape.*—Most commonly elliptical to linear.

*Apex.*—Acute.

*Base.*—Cuneate.

Reproductive organs: None; center of bloom only with vegetative growth.

Receptacle:

*Surface.*—Glaucous, typically with limited numbers of fine hairs and stipitate glands present.

*Color.*—RHS 144A (Yellow-Green).

*Shape.*—Funnel-shaped.

*Texture.*—Occasionally glabrous, generally papillate.

*Size.*—5.0 mm in height and 8.0 mm in width.

Hips and seed formation: None observed.

Disease resistance: Above average resistance to Powdery mildew (*Sphaerotheca pannosa*) and *Botrytis* (*Botrytis cinerea*) diseases under normal growing conditions in Jackson County, Oreg.

COMPARISON WITH PARENTAL LINES

The new rose plant may be distinguished from its seed or female parent, an un-named seedling, by the following combination of characteristics:

1. 'KORpot044' has white flowers, whereas the un-named seedling has apricot-colored flowers.
2. 'KORpot044' has a larger number of medium-sized flowers, whereas the un-named seedling has a smaller number of large-sized flowers.

The new rose plant may be distinguished from its pollen or male parent, an un-named seedling, by the following combination of characteristics:

1. 'KORpot044' has white flowers, whereas the un-named seedling has copper yellow flowers.
2. 'KORpot044' has semi-glossy foliage, whereas the un-named seedling has glossy foliage.

COMPARISON WITH COMMERCIAL LINE

For a comparison, several physical characteristics of the rose variety 'KORpot001', (U.S. Plant Pat. No. 23,954 and issued on Oct. 8, 2013) are compared to 'KORpot044' in Chart 1.

CHART 1

| Characteristic | 'KORpot044' | 'KORpot001' |
|---|---|---|
| Flower size. | Medium for a miniature rose, 50.0 mm to 60.0 mm in diameter. | Large for a miniature rose, 80.0 mm in diameter. |
| Petal Count | Approximately 115 to 120 petals under normal conditions. | Approximately 70 to 85 petals under normal conditions. |
| General Tonality | On open flower, RHS 155C (White) | On open flower, RHS 20C (Yellow-Orange) |

I claim:

1. A new and distinct variety of rose plant named 'KORpot044' as illustrated and described herein.

* * * * *